United States Patent [19]

O'Mant

[11] 3,960,893

[45] *June 1, 1976

[54] PHENYL-THIENYL-ALKANOIC ACID DERIVATIVES AND PHENYL-FURYL-ALKANOIC ACID DERIVATIVES

[75] Inventor: Derrick Michael O'Mant, Macclesfield, England

[73] Assignee: Imperial Chemical Industries Limited, London, England

[ * ] Notice: The portion of the term of this patent subsequent to Nov. 11, 1991, has been disclaimed.

[22] Filed: June 28, 1973

[21] Appl. No.: 374,782

Related U.S. Application Data

[60] Continuation of Ser. No. 53,007, July 7, 1970, abandoned, which is a division of Ser. No. 812,358, April 1, 1969, abandoned.

[30] Foreign Application Priority Data

| Apr. 16, 1968 | United Kingdom | 17895/68 |
| Oct. 25, 1968 | United Kingdom | 50788/68 |
| Dec. 10, 1968 | United Kingdom | 58666/68 |

[52] U.S. Cl. .................. 260/332.2 A; 260/347.3; 260/347.4; 424/275; 424/285
[51] Int. Cl.$^2$ .................................. C07D 333/24
[58] Field of Search ............... 260/332.2 A, 347.3, 260/347.4

[56] References Cited
UNITED STATES PATENTS
3,560,525   2/1971   Kaltenbronn .................... 260/332.2

*Primary Examiner*—Natalie Trousof
*Assistant Examiner*—C. M. S. Jaisle
*Attorney, Agent, or Firm*—Cushman, Darby & Cushman

[57] ABSTRACT

Phenyl-thienyl-alkanoic acid derivatives and phenyl-furyl-alkanoic acid derivatives, processes for their preparation, and pharmaceutical compositions comprising them. Compounds have anti-inflammatory, hypocholesterolaemic, analgesic and antipyretic activity. A representative compound is α-(4-bromo-5-p-chlorophenyl-thien-2-yl)acetic acid.

3 Claims, No Drawings

PHENYL-THIENYL-ALKANOIC ACID DERIVATIVES AND PHENYL-FURYL-ALKANOIC ACID DERIVATIVES

This is a continuation of application Ser. No. 53,007, filed July 7, 1970, which is a division of Ser. No. 812,358, filed April, 1969, now both abandoned.

This invention relates to new heterccyclic compounds, and more particularly it relates to new thiophen and furan derivatives which have anti-inflammatory, hypochloesterolaemic, analgesic and antipyretic acitivity.

According to the invention there are provided heterocyclic compounds of the formula:

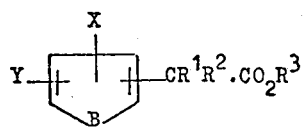

wherein B stands for an oxygen or sulphur atom, X stands for hydrogen or a chlorine or bromine atom, Y stand for a phenyl radical, optionally substituted by one or two fluorine, chlorine or bromine atom(s), and $R^1$ and $R^2$ are the same or different and either stands for hydrogen or a methyl radical, and $R^3$ stands for hydrogen or a $C_{1-5}$ alkyl, benzyl or phenyl radical, and Y and $—CR^1R^2.CO_2R^3$ are linked to non-adjacent carbon atoms of the heterocyclic nucleus, and when X stands for hydrogen $R^1$ stands for a methyl radical, and non-toxic pharmaceutically-acceptable salts of said compounds wherein $R^3$ stands for hydrogen.

As stated above, in the compounds of this invention Y and $—CR^1R^2.CO_2R^3$ are linked to non-adjacent carbon atoms of the heterocyclic nucleus. It is to be understood that this situation obtains generally throughout this specification. Thus, in the heterocyclic compounds used as starting materials in the processes disclosed below Y and $—CR^1R^2.CO_2R^3$ (or groups corresponding to the latter) are linked to non-adjacent carbon atoms of the heterocyclic nucleus.

Compounds wherein Y contains one or two halogeno substituent(s), as described above, constitute a preferred embodiment of the invention because, generally speaking, they are more active than the corresponding unsubstituted phenyl derivatives.

As a suitable value for $R^3$ there may be mentioned, for example, hydrogen or a methyl, ethyl, propyl, butyl, benzyl or phenyl radical. Suitable salts in the case where $R^3$ stands for hydrogen are salts containing a non-toxic pharmaceutically-acceptable cation; examples are salts with alkali metals or alkaline earth metals, and aluminum and ammonium salts, and salts with non-toxic pharmaceutically-acceptable organic bases, for example triethanolamine.

A preferred compound of the invention is α-(4-bromo-5p-chlorophenylthien-2-yl)acetic acid.

Those of the said compounds of formula I in which $R^3$ stands for a $C_{1-5}$ alkyl radical may be obtained by reacting a compound of the formula:

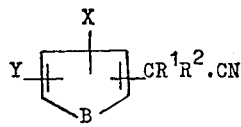

wherein B, X, Y, $R^1$ and $R^2$ have the meanings stated above, with a $C_{1-5}$ alkanol in the presence of sulphuric or hydrochloric acid, provided that when B stands for an oxygen atom the acid must be hydrochloric acid. When B stands for an oxygen atom the reaction should not be carried out under the influence of heat. On the other hand, when B stands for a sulphur atom, the reaction may optionally be carried out under the influence of heat.

Those of the said compounds of formula I in which $R^3$ stands for hydrogen may be obtained by hydrolysing a compound of the formula:

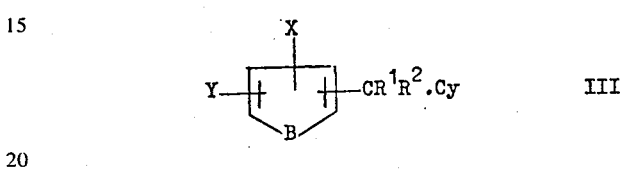

wherein B, X, Y, $R^1$ and $R^2$ have the meanings stated above and Cy stands for a cyano, carbamoyl, ($—CONH_2$), thiocarbamoyl ($—CSNH_2$), $C_{2-6}$ alkoxycarbonyl, benzyloxycarbonyl or phenoxycarbonyl radical. A suitable hydrolytic agent in the case where Cy stands for a cyano, carbamoyl or thiocabamoyl radical is an alkali metal hydroxide. A suitable hydrolytic agent in the case where Cy stands for a $C_{2-6}$ alkoxycarbonyl, benzloxycarbonyl or phenoxycarbonyl radical is an alkali metal hydroxide or (only in the case where B stands for a sulphur atom) an inorganic acid.

Those of the said compounds of formula I in which $R^3$ stands for a $C_{1-5}$ alkyl, benzyl or phenyl radical may be obtained by esterifying the corresponding carboxylic acid, carboxylic acid halide or carboxylic acid anhydride. The esterification may be carried out by known general methods. It is to be understood that when B stands for an oxygen atom and the esterification is carried out under acidic conditions, the conditions must be mild ones.

Those of the said compounds of formula I wherein $R^1$ stands for a methyl radical and $R^3$ stands for a $C_{1-5}$ alkyl, benzyl or phenyl radical, may be obtained by reacting an alkali metal derivative of a compound of the formula:

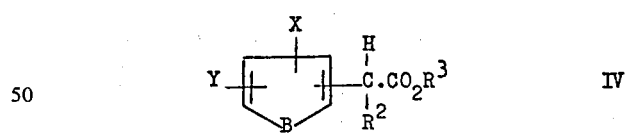

wherein B, X, Y and $R^2$ have the meanings stated above and $R^3$ has the meaning stated immediately above, with methyl chloride, bromide or iodide. This process is conveniently carried out in an organic solvent, for example dimethyl sulphoxide or dioxan. By means of this process there may be obtaned α-monomethyl derivatives [i.e. $-CH_2.CO_2R^3$ is converted into $—CH(CH_3)-.CO_2R^3$] or α,α-dimethyl derivatives [i.e. $—CH_2.CO_2R^3$ or $—CH(CH_3).CO_2R^3$ is converted into $—C(CH_3)_2-.CO_2R^3$].

Those of the said compounds of formula I wherein $R^2$ and $R^3$ stand for hydrogen may be obtained by reacting a compound of the formula:

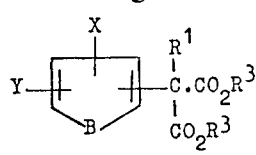

wherein B, X, Y and R¹ have the meanings stated above, and R³ stands for a C₁₋₅ alkyl, benzyl or phenyl radical, with an inorganic base in the presence of water and under the influence of heat or (only in the case where B stands for a sulphur atom) with an inorganic acid in the presence of water and under the influence of heat. A suitable inorganic base is an alkali metal hydroxide. The reaction may optionally be carried out in the presence of an organic solvent, for example ethanol.

Those of the said compounds of formula I in which X stands for a chlorine or bromine atom and R³ stands for a C₁₋₁₅ alkyl, benzyl or phenyl radical may be obtained by reacting the corresponding compound wherein X stands for hydrogen, in the presence of an alkali metal acetate, with a solution of chlorine or bromine in an organic solvent, for example acetic acid.

It is to be understood that the starting materials used in all the above processes are obtainable by methods known per se. Also, the non-toxic pharmaceutically-acceptable salts of the invention are obtainable by methods known per se.

According to a further feature of the invention there are provided pharmacetical compositions comprising a heterocyclic compound of the formula I, wherein B, X, Y, R¹, R² and R³ have the meanings stated above, or a non-toxic pharmaceutically-acceptable salt of a said compound wherein R³ stands for hydrogen, and a non-toxic pharmaceutically-acceptable diluent or carrier.

The pharmaceutical compositions may, for example, be in the form of tablets, pills, capsules, suppositories, non-sterile aqueous or non-aqueous solutions or suspensions, sterile injectable aqueous or non-aqueous solutions or suspensions, creams, lotions, or ointments. These compositions may be obtained in conventional manner using conventional excipients. The compositions may optionally contain, in addition to at least one of the heterocyclic compounds which characterise this invention, at least one known agent having anti-inflammatory and/or analgesic activity, for example aspirin, paracetamol, codeine, chlorquine, phenylbutazone, oxyphenbutazone, indomethacin, mefenamic acid, flufenamic acid, ibufenac, or an anti-inflammatory steroid, for example prednisolone. Those compositions intended for oral administration may, in addition, optionally contain at least one anti-cholinergic agent, for example homatropine methyl bromide, and/or an antacid, for example aluminium hydroxide; and/or a uricosuric agent, for example probenecid. Those compositions designed for topical application may, in addition, optionally contain a vasodilating agent, for example tolazoline, or a vasoconstricting agent, for example adrenaline; a local anaesthetic, for example amethocaine, or a counter-irritant, for example capsicum; and/or at least one agent chosen from the following classes: antibacterial agents, which include sulphonamides and antibiotics having antibacterial action, for example neomycin; antifungal agents, for example hydroxyquinoline; anti-histaminic agents, for example promethazine; and rubefacient agents, for example methyl nicotinate.

The compounds of the invention are active in a test (Adjuvant induced arthritis in rats; Newbould, Brit. J. Pharmacol. Chemotherap., 1963, 21, 127–136) which is standard in the art for testing for anti-inflammatory activity. It is well known and accepted in the art that non-steroidal anti-inflammatory compounds exhibit analgesic and anti-pyretic activity. Accordingly, as the compounds of the invention are non-steroidal anti-inflammatory compounds, it is reasonable to conclude that they possess analgesic and antipyretic activity.

The compounds of the invention are useful in the treatment of warm-blooded animals (including mammals) and for this purpose we recommend that one of said compounds be administered orally as a suitable dosage unit form, for example a tablet or capsule, and that the daily dosage be in the range 0.75 to 15 mg. per kg. of host. In particular, when one of said compounds is used for the treatment of man we recommend that it be administered orally as a suitable dosage unit form, for example a tablet or capsule, at a total daily dose of 50 to 1000 mg. of said compound per 70 kg. man.

The invention is illustrated but not limited by the following Examples:

EXAMPLE 1

2-(α-cyanoethyl-5-p-chlorophenylthiophen (2g.) was refluxed with methanol (100 ml.), concentrated sulphuric acid (40 ml.) and water (1 ml.) for 5 hours. The resulting solution was poured into water (500 ml.) and extracted with ether (3 × 250 ml.). The ethereal extract was dried (anhydrous sodium sulphate) and evaporated in vacuo to an oil, which was purified by chromatography on a column of magnesium silicate eluted with benzene. The solvent was evaporated from the eluate, and there was thus obtained methyl α(5-p-chlorophenylthien-2-yl)-propionate. This ester was hydrolysed by heating it with ethanol (50 ml.) and N-sodium hydroxide (50 ml.) for 30 minutes. The mixture was cooled, diluted with water (300 ml.), and washed with ether (2 × 100 ml.). The aqueous layer was acidified with hydrochloric acid and the precipitated solid was collected by filtration and crystallised from chloroform. There was thus obtained α-(5-p-chlorophenylthien-2-yl)propionic acid, m.p. 150°–151°C.

The cyanoethylthiophen derivative used as starting material (m.p. 74°–75°C.) was obtained from 2-acetyl-5-p-chlorophenylthiophen by conventional means.

EXAMPLE 2

Methyl 5-p-chlorophenylthien-2-ylacetate (5.32 g.) was stirred with a mixture of glacial acetic acid (100 ml.) and sodium acetate (4.8 g.). A solution of bromine (1 ml.) in glacial acetic acid (15 ml.) was added. The mixture was stirred for two hours and then poured into ice/waer (1 l.). After 4 days at ambient temperature the mixture was extracted with ether (4 × 200 ml.), the combined ethereal extracts were successively washed with water (3 × 200 ml.), 10% w/v aqueous sodium bicarbonate (2 × 200 ml.), and water (200 ml.), dried over anhydrous sodium sulphate, and evaporated to give a pale yellow oil. Part of this oil (1.75 g.) was refluxed with ethanol (15 ml.), water (40 ml.) and 11N-sodium hydroxide (15 ml.) for 3 hours. The mixture was added to ice/water (100 ml.) and extracted with ether (3 × 20 ml.). The aqueous layer was acidified with 2N-acetic acid and extracted with ether (3 × 20 ml.). The combined ethereal extracts were washed with water (2 × 20 ml.), dried over anhydrous sodium sulphate and evaporated in a relatively high vacuum (0.5 mm.). The residual solid was dissolved in the minimum volume of ether, and after the addition of 4 volumes of petroleum ether (b.p. 60°–80°C.), gave crystals of α-(4-bromo-5-p-chlorophenylthien-2-yl)acetic acid, m.p. 136°–137°C.

EXAMPLE 3

Methyl 5-p-chlorophenylthien-2-ylacetate (1 g.) was dissolved in dry dioxan (10 ml.). Sodium hydride (0.1 g.) was added, the mixture was stirred for 30 minutes, and methyl iodide (0.6 g.) was then added. The mixture was refluxed for 30 minutes, cooled, and further sodium hydride (0.1 g.) and methyl iodide (1.1 ml.) were added. The mixture was refluxed for 2 hours, cooled and evaporated in vacuo to give an oil which was chromatographed on a column of Florisil (column: 9 inches long × 1 inch diameter) which was eluted with a mixture of equal volumes of benzene and petroleum ether (b.p. 60°–80°C.). The first 350 ml. of eluate was evaporated in vacuo to give an oil. This oil, which was mainly methyl α,α-dimethyl-α-(5-p-chlorophenylthien-2-yl)acetate, was hydrolysed by conventional means and gave α,α-dimethyl-α-(5-p-chlorophenylthien-2yl)-acetic acid, m.p. 146°–148°C.

EXAMPLE 4

Dimethyl α(5-p-chlorophenylthien-2-yl)-α-methyl-malonate (0.05 g.) was heated at 95°C. for 3 hours with 8N-sodium hydroxide (4 ml.). After cooling, the mixture was acidified with glacial acetic acid to pH 4.5 and extracted with ether (3 × 10 ml.). The ether extracts were dried over anhydrous sodium sulphate and evaporated in vacuo to give a solid which was α-(5-p-chlorophenylthien-2-yl)-propionic acid, m.p. 150°–151°C.

EXAMPLE 5

To a stirred mixture of 20 parts of steric acid, 15 parts of arachis oil, 5 parts of liquid paraffin and 0.5 part of cetostearyl alcohol heated at 65°C. there was added a solution at 60°C. prepared from 5 parts of α-(4-bromo-5-p-chlorophenylthien-2-yl)acetic acid, 0.75 part of triethanolamine and 53.75 parts of water, and stirring was continued after mixing while the temperature was allowed to fall to 40°C. The mixture was then homogenised by passage through a colloid mill and there was thus obtained a vanishing cream suitable for topical application for therapeutic purposes.

What we claim is:

1. A heterocyclic compound of the formula:

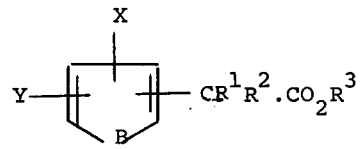

wherein B stands for an oxygen or sulphur atom, X stands for hydrogen or a chlorine or bromine atom, Y stands for phenyl or phenyl substituted by fluorine, chlorine or bromine atom, and $R^1$ and $R^2$ are the same or different and either stands for hydrogen or a methyl radical, and $R^3$ stands for hydrogen or a $C_{1-5}$ alkyl, benzyl or phenyl radical, and Y and $-CR^1R^2.CO_2R^3$ and linked to non-adjacent carbon atoms of the heterocyclic nucleus, and when X stands for hydrogen, $R^1$ stands for a methyl radical, and non-toxic pharmaceutically-acceptable salts of said compounds wherein $R^3$ stands for hydrogen.

2. A heterocyclic compound according to claim 1 wherein X is chlorine or bromine.

3. A compound as claimed in claim 1 which is α-(4-bromo-5-p-chlorophenylthien-2-yl)acetic acid.

* * * * *